United States Patent [19]
Long et al.

[11] Patent Number: 6,107,319
[45] Date of Patent: Aug. 22, 2000

[54] OXAZOLINE ARTHROPODICIDES

[75] Inventors: Jeffrey Keith Long, Wilmington; Thomas Martin Stevenson, Newark, both of Del.

[73] Assignee: E. I. du Pont de Nemours and Company, Wilmington, Del.

[21] Appl. No.: 09/101,925

[22] PCT Filed: Jan. 7, 1997

[86] PCT No.: PCT/US97/00268
§ 371 Date: Jul. 15, 1998
§ 102(e) Date: Jul. 15, 1998

[87] PCT Pub. No.: WO97/26249
PCT Pub. Date: Jul. 24, 1997

Related U.S. Application Data

[60] Provisional application No. 60/010,014, Jan. 16, 1996.

[51] Int. Cl.$^7$ .................. C07D 263/10; C07D 263/14; A01N 43/74
[52] U.S. Cl. .................. 514/374; 548/236; 548/237; 548/239
[58] Field of Search .................. 548/236, 237, 548/239; 514/374

[56] References Cited

FOREIGN PATENT DOCUMENTS

| | | |
|---|---|---|
| 0 432 661 | 6/1991 | European Pat. Off. . |
| 0 645 085 A1 | 3/1995 | European Pat. Off. . |
| 0 686 345 | 12/1995 | European Pat. Off. . |
| 195 23 388 A1 | 4/1996 | Germany . |
| WO 95 04726 | 2/1995 | WIPO . |
| WO 95/19350 | 7/1995 | WIPO . |
| WO 96 22283 | 7/1996 | WIPO . |

Primary Examiner—Mukund J. Shah
Assistant Examiner—Brenda Coleman

[57] ABSTRACT

Compounds of Formula I, and their agriculturally-suitable salts, are disclosed which are useful as arthropodicides

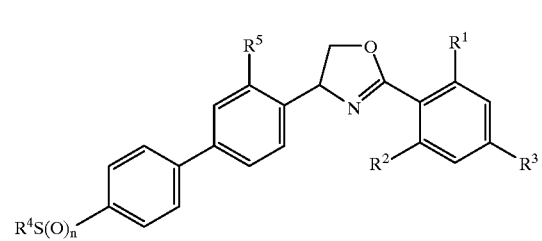

wherein $R^1$–$R^5$ and n are as defined in the disclosure.

Also disclosed are compositions containing the compounds of Formula I and a method for controlling arthropods which involves contacting the arthropods or their environment with an effective amount of a compound of Formula I.

17 Claims, No Drawings

OXAZOLINE ARTHROPODICIDES

CROSS-REFERENCE TO RELATED APPLICATIONS

This application is a national stage entry under 35 U.S.C. §317 of PCT/US97/00268, filed Jan. 7, 1997 which claims the benefit of U.S. Provisional Application Ser. No. 60/010,014 filed Jan. 16, 1996.

BACKGROUND OF THE INVENTION

This invention relates to certain oxazolines, their agriculturally suitable salts and compositions, and methods of their use as arthropodicides in both agronomic and nonagronomic environments.

The control of arthropod pests is extremely important in achieving high crop efficiency. Arthropod damage to growing and stored agronomic crops can cause significant reduction in productivity and thereby result in increased costs to the consumer. The control of arthropod pests in forestry, greenhouse crops, ornamentals, nursery crops, stored food and fiber products, livestock, household, and public and animal health is also important. Many products are commercially available for these purposes, but the need continues for new compounds which are more effective, less costly, environmentally safer, less toxic or have different modes of action.

WO 95/04726 generically discloses compounds of Formula i:

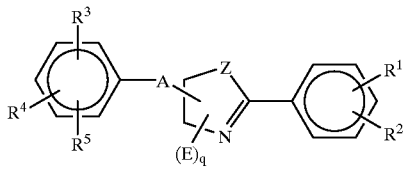

i wherein:
  A is selected from the group a direct bond and $C_1$–$C_3$ straight or branched chain alkylene;
  E is selected from the group $C_1$–$C_4$ alkyl and $C_1$–$C_4$ haloalkyl;
  Z is selected from the group O and S; and
  $R^1$ and $R^2$ are independently selected from the group H, halogen, $C_1$–$C_6$ alkyl, $C_1$–$C_6$ haloalkyl, $C_1$–$C_6$ haloalkoxy, $C_1$–$C_6$ alkylthio, CN and $NO_2$.

Compounds of the present invention are unexpectedly more effective, environmentally safer and less toxic than those named in WO 95/04726.

SUMMARY OF THE INVENTION

This invention is directed to compounds of Formula I including all geometric and stereoisomers, agriculturally suitable salts thereof, agricultural compositions containing them and their use as arthropodicides:

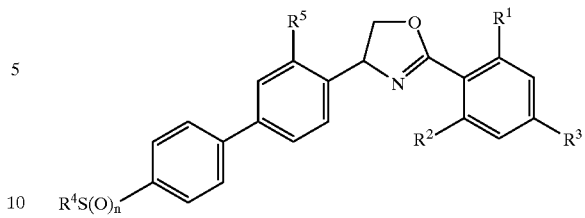

I wherein:
  $R^1$ is H, F, or Cl;
  $R^2$ is F or Cl;
  $R^3$ is H or F;
  $R^4$ is $C_1$–$C_2$ haloalkyl;
  $R^5$ is H, F, Cl, $C_1$–$C_2$ alkyl, or $C_1$–$C_2$ alkoxy; and
  n is 0, 1, or 2;
provided that
  i) when $R^2$ is F, $R^3$ and $R^5$ are H, and n is 0, then $R^4$ is other than $CF_3$; and
  ii) when $R^1$ is F, $R^2$ is Cl, $R^3$ and $R^5$ are H, and n is 0, then $R^4$ is other than $CF_3$.

In the above recitations, the term "alkyl", used either alone or in compound words such as "haloalkyl" includes methyl and ethyl. "Alkoxy" includes methoxy and ethoxy.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

The total number of carbon atoms in a substituent group is indicated by the "$C_i$–$C_j$" prefix where i and j are numbers from 1 to 2. For example, $C_1$–$C_2$ alkyl designates methyl and ethyl and $C_1$–$C_2$ alkoxy designates $CH_3O$ and $CH_3CH_2O$.

When a group contains a substituent which can be hydrogen, for example $R^1$ or $R^5$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic group.

Preferred compounds for reasons of better activity, environmental safety, less toxicity and/or ease of synthesis are:

Preferred 1. Compounds of Formula I above, and agriculturally suitable salts thereof, wherein:

$R^1$ and $R^2$ are F;

$R^3$ is H; and $R^4$ is $CF_2H$, $CF_3$, $CF_2Br$, $CF_2CF_2H$, or $CF_2CF_3$.

Preferred 2. Compounds of Formula I above, and agriculturally suitable salts thereof, wherein:

$R^1$, $R^2$ and $R^3$ are F; and $R^4$ is $CF_2H$, $CF_3$, $CF_2Br$, $CF_2CF_2H$, or $CF_2CF_3$.

Preferred 3. Compounds of Formula I above, and agriculturally suitable salts thereof, wherein:

$R^1$ is H;

$R^2$ is Cl; and $R^5$ is H.

Most preferred are compounds of Preferred 3 selected from the group:

2-(2-chlorophenyl)-4-[4'-[(difluoromethyl)thio][1,1'-biphenyl]-4-yl]-4,5-dihydrooxazole;

2-(2-chlorophenyl)-4-[4'-[(difluoromethyl)sulfinyl][1,1'-biphenyl]-4-yl]-4,5-dihydrooxazole; and 2-(2-chlorophenyl)-4-[4'-[(difluoromethyl)sulfonyl][1,1'-biphenyl]-4-yl]-4,5-dihydrooxazole.

Preferred 4. Compounds of Preferred 1 wherein:

$R^5$ is H.

Preferred 5. Compounds of Preferred 4 wherein:

$R^4$ is $CF_2H$, $CF_3$ or $CF_2Br$.

Most preferred are compounds of Preferred 5 selected from the group:

4-[4'-[(difluoromethyl)thio][1,1'-biphenyl]-4-yl]-2-(2,6-difluorophenyl)-4,5-dihydrooxazole;

4-[4'-[(difluoromethyl)sulfinyl][1,1'-biphenyl]-4-yl]-2-(2,6-difluorophenyl)-4,5-dihydrooxazole;

4-[4'-[(difluoromethyl)sulfonyl][1,1'-biphenyl]-4-yl]-2-(2,6-difluorophenyl)-4,5-dihydrooxazole;

(−)-4-[4'-[(difluoromethyl)thio][1,1'-biphenyl]-4-yl]-2-(2,6-difluorophenyl)-4,5-dihydrooxazole;

the sulfoxide of (−)-4-[4'-[(difluoromethyl)thio][1,1'-biphenyl]-4-yl]-2-(2,6-difluorophenyl)-4,5-dihydrooxazole wherein the sulfoxide has the S configuration;

the sulfoxide of (−)-4-[4'-[(difluoromethyl)thio][1,1'-biphenyl]-4-yl]-2-(2,6-difluorophenyl)-4,5-dihydrooxazole wherein the sulfoxide has the R configuration; and the sulfone of (−)-4-[4'-[(difluoromethyl)thio][1,1'-biphenyl]-4-yl]-2-(2,6-difluorophenyl)-4,5-dihydrooxazole.

This invention also relates to arthropodicidal compositions comprising arthropodicidally effective amounts of the compounds of Formula I and at least one of a surfactant, a solid diluent or a liquid diluent. The preferred compositions of the present invention are those which comprise the above preferred compounds.

This invention also relates to a method for controlling arthropods comprising contacting the arthropods or their environment with an arthropodicidally effective amount of the compounds of Formula I (e.g., as a composition described herein). The preferred methods of use are those involving the above preferred compounds.

DETAILS OF THE INVENTION

The compounds of Formula I can be prepared by one or more of the following methods and variations as described in Schemes 1–3. The definitions of $R^1$–$R^5$ and n in the compounds of Formulae I–VII below are as defined above in the Summary of the Invention.

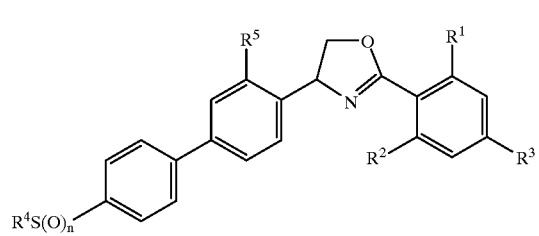

The compounds of Formula I used as effective ingredients in this invention can, for example, be prepared by the steps shown in the following reaction schemes with compounds of Formula II. Intermediates of Formula II (e.g., 2-(2,6-difluorophenyl)-4,5-dihydro-4-(4-iodophenyl)oxazole which is the compound of Formula II where $R^1$=F, $R^2$=F, $R^3$=H, $R^5$=H, and $R^{20}$=I) can be prepared by the methods described in WO 95/04726. The reaction of Scheme 1 is carried out at −78° C. to the boiling point of an inert solvent selected from tetrahydrofuran (THF), ethyl ether, hexane, toluene, etc., for 30 min to 72 h with a transition metal catalyst, for example, bis(1,2-diphenylphosphinoethane) nickel(II) chloride, tetrakis(triphenylphosphine)palladium (0), bis(triphenylphosphine)palladium(II) chloride, or palladium(II) acetate with, for example, tri-ortho-tolylphosphine or triphenylarsine, and with or without the presence of added cofactors, for example, lithium chloride, copper(I) iodide, or dialkyl- or trialkylamines, to give compounds of Formula IV.

Scheme 1

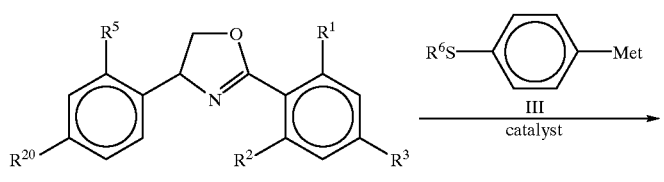

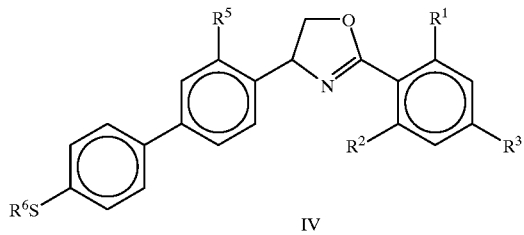

IV $R^6 = R^4$ or a protecting group,
$R^{20} = I, Br, OSO_2CF_3, OSO_2F$, etc.,
Met = MgX, ZnX(X = Cl, Br, I),
$SnMe_3, SnBu_3, B(OH)_2$, etc.

Intermediates of Formula III are prepared by procedures known in the art. $R^6$ can be equal to $R^4$, in which case compounds of Formula I are obtained directly, or $R^6$ can be, as needed for ease of synthesis, a sulfur-protecting group such as, for example, t-butyldimethylsilyl, t-butyl, p-methoxybenzyl, etc.

If $R^6$ is a protecting group, compounds of Formula I are prepared by deprotection of the sulfur and further reaction, as in Scheme 2. The reactions of intermediates of Formula V are carried out in an optional, inert solvent selected from tetrahydrofuran (THF), dioxane, ethyl ether, dichloromethane, hexane, toluene, etc., for 5 min to 72 h at −20° C. to the boiling point of the solvent. Reaction with a hydrohalocarbon, such as chlorodifluoromethane, chloroform, etc., and a base, such as sodium hydroxide, potassium hydroxide, potassium t-butoxide, etc., optionally in the presence of a phase-transfer catalyst, or, alternatively, with a hydrohalo- or halocarbon substituted with a leaving group, such leaving group being iodide, bromide, chloride, methanesulfonate, p-toluenesulfonate, etc., optionally in the presence of a base, for example, sodium hydride, sodium hydroxide, potassium hydroxide, potassium t-butoxide, etc., and optionally in the presence of a phase-transfer catalyst gives compounds of Formula I. A compound of Formula V can alternatively react with an activated alkene, such as tetrafluoroethylene, in the presence of an optional basic, acidic, or radical catalyst. Alternatively, the mercaptan of Formula V can be oxidized to a disulfide (see p. 1092 of *Advanced Organic Chemistry*, 3rd edition, J. March, (1985), John Wiley & Sons, New York) and converted to a compound of Formula I by reaction with perhaloalkanes and a radical initiator (see, for example, C. Wakselman, et al, *J. Chem Soc., Chem. Commun.*, (1991), 993).

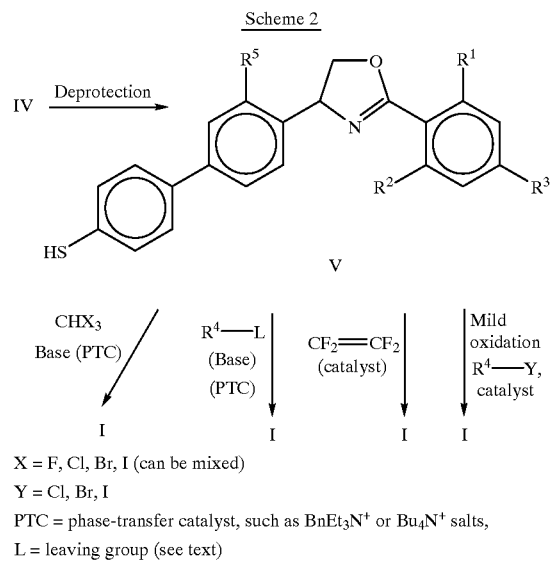

X = F, Cl, Br, I (can be mixed)
Y = Cl, Br, I
PTC = phase-transfer catalyst, such as $BnEt_3N^+$ or $Bu_4N^+$ salts,
L = leaving group (see text)

Compounds of Formula I are also prepared as in Scheme 3. A compound of Formula II is converted to a stannyl derivative of Formula VI by its reaction with, for example, hexamethyldistannane under catalysis by a metal complex, such as tetrakis(triphenylphosphine)palladium(0), bis (triphenylphosphine)palladium(II) chloride, or palladium (II) acetate with, for example, tri-ortho-tolylphosphine, triphenylarsine, etc., with or without the presence of added cofactors, for example, lithium chloride, copper(I) iodide, dialkyl- or trialkylamines, etc. The stannyl derivative of Formula VI is then reacted with a substituted aromatic derivative of Formula VII in the presence of a catalytic metal complex such as those noted above to afford a compound of Formula IV which again is a compound of Formula I ($R^6=R^4$) or, if $R^6$ is a protecting group, can then be converted by the chemistry of Scheme 2 to a compound of Formula I.

Scheme 3

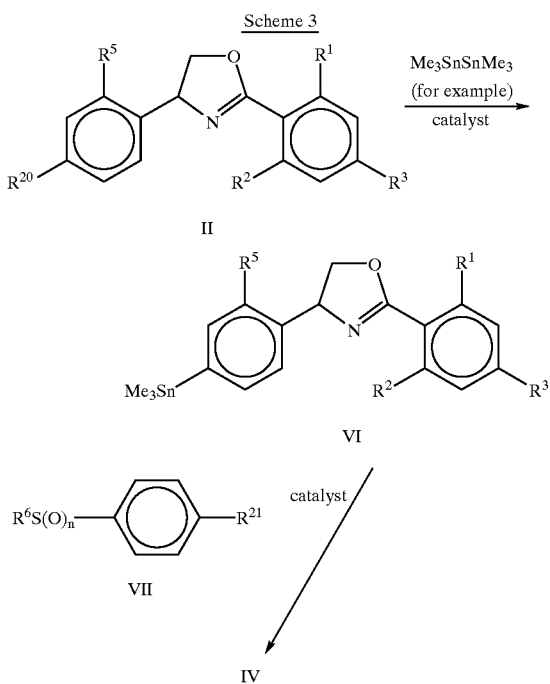

$R^6 = R^4$ or a protecting group,
$R^{20}$ = as defined in Scheme 1,
$R^{21}$ independently equals groups defined for $R^{20}$,
n = 0, 1, 2.

The compounds of Formula I in which n=1 or 2 are prepared from compounds of Formula I in which n=0 by the action of mild oxidants, for example, organic peracids, sodium periodate, etc. (see, for example, March, cited previously, pp. 1089–1090, etc.). Alternatively, intermediates such as those of Formula VII, for example, in which n=1 or 2, give products of Formula I with n=1 or 2 by the chemistry of Scheme 3.

The desired product can be prepared by carrying out conventional post-reaction procedures, such as extraction, filtration, and concentration, and if needed further purified appropriately by such means as chromatography and/or crystallizations.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Example is, therefore, to be construed as merely illustrative, of the disclosure. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; m=multiplet.

EXAMPLE 1

Step A: Preparation of [(4-bromophenyl)thio]tris(1-methylethyl)silane

To a solution of 45 grams of 4-bromothiophenol in 250 mL of THF was added 53 mL of triisopropylsilyl chloride and 38 mL of DBU (1,8-diazabicyclo[5.4.0]undec-7-ene) under a nitrogen atmosphere. The reaction mixture heated spontaneously to reflux. The reaction mixture was allowed to cool and was diluted with 500 mL of hexanes. The resultant white suspension was filtered through a pad of Celite® (diatomaceous earth), and the filter cake was washed with additional hexanes and 100 mL of ether. The filtrate was washed with ice-cold 0.1 N aqueous HCl, water, aqueous NaHCO$_3$, and saturated aqueous NaCl, dried over MgSO$_4$, and concentrated under vacuum to obtain 82 grams of the title compound of Step A as a clear oil. $^1$H NMR (CDCl$_3$, 300 MHz) δ 1.1 (m, 18H), 1.2 (m, 3H), 7.3–7.4 (m, 4H).

Step B: Preparation of 2-(2,6-difluorophenyl)-4,5-dihydro-4-[4'-[[tris(1-methylethyl)silyl]thio][1,1'-biphenyl]-4-yl]oxazole The title compound of Step A (4.3 g) was dissolved in 15 mL of THF under a nitrogen atmosphere and the reaction mixture was cooled below −65° C. and then 4.7 mL of 2.5 M n-BuLi/hexanes solution was added dropwise. After 15 minutes, 26 mL of 0.5 M ZnCl$_2$/THF solution was added dropwise. In a separate reaction flask, 67 mg of Pd(OAc)$_2$ was added to a solution of 201 mg of tri(o-tolyl)phosphine in 5 mL of THF, and this mixture was stirred for 5 minutes before its addition, via cannula, to the main reaction mixture. A solution of 3.85 g of 2-(2,6-difluorophenyl)-4,5-dihydro-4-(4-iodophenyl)oxazole (prepared as described in WO 95/04726) in 10 mL of THF was added, and the reaction mixture was allowed to warm to room temperature and stir for 2 to 3 hours. The reaction mixture was poured into ice-cold aqueous NH$_4$Cl and extracted with ethyl acetate. The organic phase was washed with saturated aqueous NaCl, dried over MgSO$_4$, and concentrated under vacuum. The oily residue was adsorbed onto silica gel, applied to a column of silica gel and eluted with hexane/ethyl acetate (6:1 v:v) to obtain 3.6 g of the title compound of Step B as a viscous oil. $^1$H NMR (CDCl$_3$, 300 MHz) δ 1.1 (m, 18H), 1.3 (m, 3H), 4.3 (m, 1H), 4.8 (m, 1H), 5.5 (m, 1H), 7.0 (m, 2H), 7.3–7.5 (m, 5H), 7.5–7.6 (m, 4H).

Step C: Preparation of 4-[4'-[(difluoromethyl)thio][1,1'-biphenyl]-4-yl]-2-(2,6-difluorophenyl)-4,5-dihydrooxazole To a solution of 10.9 g of the title compound of Step B in 20 mL of THF was added 23 mL of a commercial 1.0 M solution of n-Bu$_4$NF in THF (containing 5% water) at 15 to 20° C. (water bath cooling) under a nitrogen atmosphere. After 5 minutes, 5.9 g of freshly-ground KOH was added, and then excess Freon® 22 (chlorodifluoromethane) was added through a subsurface tube at a rate sufficient to maintain a slight overpressure. After 20 to 30 minutes, the gas addition was stopped, and the reaction mixture was poured into ice-cold aqueous NH$_4$Cl and extracted with ethyl acetate. The organic phase was washed with water and saturated aqueous NaCl, dried over $MgSO_4$, and concentrated under vacuum. The residue was adsorbed onto silica gel, applied to a column of silica gel and eluted with hexanes/ethyl acetate (4:1 to 3:1 v:v) to obtain an oil. The oil crystallized upon trituration with ether and hexane to produce a white solid that was dried to provide 6.2 g of the title compound of Step C, a compound of this invention, melting at 72–76° C. $^1$H NMR ($CDCl_3$, 300 MHz) δ 4.3–4.4 (m,1H), 4.8 (m,1H), 5.5 (m,1H), 6.85 (m,1H), 7.0 (m, 2H), 7.4–7.7 (m,9H).

EXAMPLE 2

Resolution of 4-[4'-[(difluoromethyl)thio][1,1'-biphenyl]-4-yl]-2-(2,6-difluorophenyl)-4,5-dihydrooxazole A technical sample of 4-[4'-[(difluoromethyl)thio][1,1'-biphenyl]-4-yl]-2-(2,6-difluorophenyl)-4,5-dihydrooxazole (at 95% purity or better) was dissolved in hexane/isopropanol (80/20) at 10–15 mg/mL. The resulting sample solution was separated on a (S,S)-Whelk-O 1 column (a chiral column from Regis, the Pirkle-Concept chiral stationary phase is derived from (S,S)-4-(3,5-dinitrobenzamido)-tetrahydrophenanthrene covalently bound to 5 μm silica) with hexane/isopropanol (80/20) as the mobile phase. Both analytical (25 cm×4.6 mm ID, Regis catalog number 786101) and prep (25 cm×10 mm ID, Regis catalog number 786102) columns were used for this work and 500 μL or more of sample solution was injected into each column. About 10–20 mg of each enantiomer was collected within 8 hours from each column. (−)-4-[4'-[(difluoromethyl)thio][1,1'-biphenyl]-4-yl]-2-(2,6-difluorophenyl)-4,5-dihydrooxazole is the enantiomer which was eluted first (with a retention time of tR=10 minutes on the analytical column at a flow rate of 1 mL/min and with the detector set at a wavelength of 310 nm) while (+)-4-[4'-[(difluoromethyl)thio][1,1'-biphenyl]-4-yl]-2-(2,6-difluorophenyl)-4,5-dihydrooxazole is the enantiomer which was eluted second (with a time of tR=22 minutes on the analytical column at a flow rate of 1 mL/min and the detector set at a wavelength of 310 nm).

A sample of (−)-4-[4'-[(difluoromethyl)thio][1,1'-biphenyl]-4-yl]-2-(2,6-difluorophenyl)-4,5-dihydrooxazole had a rotation $[\alpha]_D^{20}$=−27.8°+/−0.9° (c 0.87, $CHCl_3$) and a melting point 71–73° C. and a sample of (+)-4-[4'-[(difluoromethyl)thio][1,1'-biphenyl]-4-yl]-2-(2,6-difluorophenyl)-4,5-dihydrooxazole had a rotation $[\alpha]_D^{20}$=+27.2°+/−2.0° (c 0.99, $CHCl_3$) and a melting point 77–78° C.

By the procedures described herein together with methods known in the art, the following compounds of Formula I in Tables 1 to 30 can be prepared. The compounds in Table 1, line 1 can be referred to as 1-1, 1-2, 1-3, and 1-4 (as designated by line and column). All the other specific compounds covered in these Tables can be designated in an analogous fashion. The following abbreviations are used in the Tables which follow: Me=methyl, Et=ethyl, OMe=methoxy, and OEt=ethoxy.

TABLE 1

$R^1$ = F, $R^2$ = F, $R^3$ = H, $R^5$ = H, n = 0, $R^4$ =

| | Column 1 | Column 2 | Column 3 | Column 4 |
|---|---|---|---|---|
| 1 | $CH_2F$ | $CHCl_2$ | $CHFCF_3$ | $CF_2CFCl_2$ |
| 2 | $CF_2H$ | $CHClCF_3$ | $CF_2CF_2H$ | $CFClCF_3$ |

TABLE 1-continued $R^1$ = F, $R^2$ = F, $R^3$ = H, $R^5$ = H, n = 0, $R^4$ =

| | Column 1 | Column 2 | Column 3 | Column 4 |
|---|---|---|---|---|
| 3 | | $CFCl_2$ | $CFClCF_2Cl$ | $CFBrCF_3$ |
| 4 | $CF_2Cl$ | $CHFCl$ | $CCl_2CF_3$ | $CH_2CF_3$ |
| 5 | $CF_2Br$ | $CFClBr$ | $CF_2CF_3$ | $CF_2CH_3$ |

TABLE 2

$R^1$ = F, $R^2$ = F, $R^3$ = H, $R^5$ = H, n = 1, $R^4$ =

| | Column 1 | Column 2 | Column 3 | Column 4 |
|---|---|---|---|---|
| 6 | $CH_2F$ | $CHCl_2$ | $CHFCF_3$ | $CF_2CFCl_2$ |
| 7 | $CF_2H$ | $CHClCF_3$ | $CF_2CF_2H$ | $CFClCF_3$ |
| 8 | $CF_3$ | $CFCl_2$ | $CFClCF_2Cl$ | $CFBrCF_3$ |
| 9 | $CF_2Cl$ | $CHFCl$ | $CCl_2CF_3$ | $CH_2CF_3$ |
| 10 | $CF_2Br$ | $CFClBr$ | $CF_2CF_3$ | $CF_2CH_3$ |

TABLE 3

$R^1$ = F, $R^2$ = F, $R^3$ = H, $R^5$ = H, n = 2, $R^4$ =

| | Column 1 | Column 2 | Column 3 | Column 4 |
|---|---|---|---|---|
| 11 | $CH_2F$ | $CHCl_2$ | $CHFCF_3$ | $CF_2CFCl_2$ |
| 12 | $CF_2H$ | $CHClCF_3$ | $CF_2CF_2H$ | $CFClCF_3$ |
| 13 | $CF_3$ | $CFCl_2$ | $CFClCF_2Cl$ | $CFBrCF_3$ |
| 14 | $CF_2Cl$ | $CHFCl$ | $CCl_2CF_3$ | $CH_2CF_3$ |
| 15 | $CF_2Br$ | $CFClBr$ | $CF_2CF_3$ | $CF_2CH_3$ |

TABLE 4

$R^1$ = F, $R^2$ = F, $R^3$ = H, $R^5$ = Me, n = 0, $R^4$ =

| | Column 1 | Column 2 | Column 3 | Column 4 |
|---|---|---|---|---|
| 16 | $CH_2F$ | $CHCl_2$ | $CHFCF_3$ | $CF_2CFCl_2$ |
| 17 | $CF_2H$ | $CHClCF_3$ | $CF_2CF_2H$ | $CFClCF_3$ |
| 18 | $CF_3$ | $CFCl_2$ | $CFClCF_2Cl$ | $CFBrCF_3$ |
| 19 | $CF_2Cl$ | $CHFCl$ | $CCl_2CF_3$ | $CH_2CF_3$ |
| 20 | $CF_2Br$ | $CFClBr$ | $CF_2CF_3$ | $CF_2CH_3$ |

TABLE 5

$R^1$ = F, $R^2$ = F, $R^3$ = H, $R^5$ = Me, n = 1, $R^4$ =

| | Column 1 | Column 2 | Column 3 | Column 4 |
|---|---|---|---|---|
| 21 | $CH_2F$ | $CHCl_2$ | $CHFCF_3$ | $CF_2CFCl_2$ |
| 22 | $CF_2H$ | $CHClCF_3$ | $CF_2CF_2H$ | $CFClCF_3$ |
| 23 | $CF_3$ | $CFCl_2$ | $CFClCF_2Cl$ | $CFBrCF_3$ |
| 24 | $CF_2Cl$ | $CHFCl$ | $CCl_2CF_3$ | $CH_2CF_3$ |
| 25 | $CF_2Br$ | $CFClBr$ | $CF_2CF_3$ | $CF_2CH_3$ |

TABLE 6

$R^1$ = F, $R^2$ = F, $R^3$ = H, $R^5$ = Me, n = 2, $R^4$ =

| | Column 1 | Column 2 | Column 3 | Column 4 |
|---|---|---|---|---|
| 26 | $CH_2F$ | $CHCl_2$ | $CHFCF_3$ | $CF_2CFCl_2$ |
| 27 | $CF_2H$ | $CHClCF_3$ | $CF_2CF_2H$ | $CFClCF_3$ |
| 28 | $CF_3$ | $CFCl_2$ | $CFClCF_2Cl$ | $CFBrCF_3$ |

TABLE 6-continued

R¹ = F, R² = F, R³ = H, R⁵ = Me, n = 2, R⁴ =

|    | Column 1 | Column 2 | Column 3 | Column 4 |
|----|----------|----------|----------|----------|
| 29 | $CF_2Cl$ | $CHFCl$  | $CCl_2CF_3$ | $CH_2CF_3$ |
| 30 | $CF_2Br$ | $CFClBr$ | $CF_2CF_3$  | $CF_2CH_3$ |

TABLE 7

R¹ = F, R² = F, R³ = H, R⁵ = Et, n = 0, R⁴ =

|    | Column 1 | Column 2 | Column 3 | Column 4 |
|----|----------|----------|----------|----------|
| 31 | $CH_2F$  | $CHCl_2$   | $CHFCF_3$   | $CF_2CFCl_2$ |
| 32 | $CF_2H$  | $CHClCF_3$ | $CF_2CF_2H$ | $CFClCF_3$   |
| 33 | $CF_3$   | $CFCl_2$   | $CFClCF_2Cl$ | $CFBrCF_3$  |
| 34 | $CF_2Cl$ | $CHFCl$    | $CCl_2CF_3$ | $CH_2CF_3$   |
| 35 | $CF_2Br$ | $CFClBr$   | $CF_2CF_3$  | $CF_2CH_3$   |

TABLE 8

R¹ = F, R² = F, R³ = H, R⁵ = Et, n = 1, R⁴ =

|    | Column 1 | Column 2 | Column 3 | Column 4 |
|----|----------|----------|----------|----------|
| 36 | $CH_2F$  | $CHCl_2$   | $CHFCF_3$   | $CF_2CFCl_2$ |
| 37 | $CF_2H$  | $CHClCF_3$ | $CF_2CF_2H$ | $CFClCF_3$   |
| 38 | $CF_3$   | $CFCl_2$   | $CFClCF_2Cl$ | $CFBrCF_3$  |
| 39 | $CF_2Cl$ | $CHFCl$    | $CCl_2CF_3$ | $CH_2CF_3$   |
| 40 | $CFBr$   | $CFClBr$   | $CF_2CF_3$  | $CF_2CH_3$   |

TABLE 9

R¹ = F, R² = F, R³ = H, R⁵ = Et, n = 2, R⁴ =

|    | Column 1 | Column 2 | Column 3 | Column 4 |
|----|----------|----------|----------|----------|
| 41 | $CH_2F$  | $CHCl_2$   | $CHFCF_3$   | $CF_2CFCl_2$ |
| 42 | $CF_2H$  | $CHClCF_3$ | $CF_2CF_2H$ | $CFClCF_3$   |
| 43 | $CF_3$   | $CFCl_2$   | $CFClCF_2Cl$ | $CFBrCF_3$  |
| 44 | $CF_2Cl$ | $CHFCl$    | $CCl_2CF_3$ | $CH_2CF_3$   |
| 45 | $CF_2Br$ | $CFClBr$   | $CF_2CF_3$  | $CF_2CH_3$   |

TABLE 10

R¹ = F, R² = F, R³ = H, R⁵ = OMe, n = 0, R⁴ =

|    | Column 1 | Column 2 | Column 3 | Column 4 |
|----|----------|----------|----------|----------|
| 46 | $CH_2F$  | $CHCl_2$   | $CHFCF_3$   | $CF_2CFCl_2$ |
| 47 | $CF_2H$  | $CHClCF_3$ | $CF_2CF_2H$ | $CFClCF_3$   |
| 48 | $CF_3$   | $CFCl_2$   | $CFClCF_2Cl$ | $CFBrCF_3$  |
| 49 | $CF_2Cl$ | $CHFCl$    | $CCl_2CF_3$ | $CH_2CF_3$   |
| 50 | $CF_2Br$ | $CFClBr$   | $CF_2CF_3$  | $CF_2CH_3$   |

TABLE 11

R¹ = F, R² = F, R³ = H, R⁵ = OMe, n = 1, R⁴ =

|    | Column 1 | Column 2 | Column 3 | Column 4 |
|----|----------|----------|----------|----------|
| 51 | $CH_2F$  | $CHCl_2$   | $CHFCF_3$   | $CF_2CFCl_2$ |
| 52 | $CF_2H$  | $CHClCF_3$ | $CF_2CF_2H$ | $CFClCF_3$   |
| 53 | $CF_3$   | $CFCl_2$   | $CFClCF_2Cl$ | $CFBrCF_3$  |
| 54 | $CF_2Cl$ | $CHFCl$    | $CCl_2CF_3$ | $CH_2CF_3$   |
| 55 | $CF_2Br$ | $CFClBr$   | $CF_2CF_3$  | $CF_2CH_3$   |

TABLE 12

R¹ = F, R² = F, R³ = H, R⁵ = OMe, n = 2, R⁴ =

|    | Column 1 | Column 2 | Column 3 | Column 4 |
|----|----------|----------|----------|----------|
| 56 | $CH_2F$  | $CHCl_2$   | $CHFCF_3$   | $CF_2CFCl_2$ |
| 57 | $CF_2H$  | $CHClCF_3$ | $CF_2CF_2H$ | $CFClCF_3$   |
| 58 | $CF_3$   | $CFCl_2$   | $CFClCF_2Cl$ | $CFBrCF_3$  |
| 59 | $CF_2Cl$ | $CHFCl$    | $CCl_2CF_3$ | $CH_2CF_3$   |
| 60 | $CF_2Br$ | $CFClBr$   | $CF_2CF_3$  | $CF_2CH_3$   |

TABLE 13

R¹ = F, R² = F, R³ = H, R⁵ = OEt, n = 0, R⁴ =

|    | Column 1 | Column 2 | Column 3 | Column 4 |
|----|----------|----------|----------|----------|
| 61 | $CH_2F$  | $CHCl_2$   | $CHFCF_3$   | $CF_2CFCl_2$ |
| 62 | $CF_2H$  | $CHClCF_3$ | $CF_2CF_2H$ | $CFClCF_3$   |
| 63 | $CF_3$   | $CFCl_2$   | $CFClCF_2Cl$ | $CFBrCF_3$  |
| 64 | $CF_2Cl$ | $CHFCl$    | $CCl_2CF_3$ | $CH_2CF_3$   |
| 65 | $CF_2Br$ | $CFClBr$   | $CF_2CF_3$  | $CF_2CH_3$   |

TABLE 14

R¹ = F, R² = F, R³ = H, R⁵ = OEt, n = 1, R⁴ =

|    | Column 1 | Column 2 | Column 3 | Column 4 |
|----|----------|----------|----------|----------|
| 66 | $CH_2F$  | $CHCl_2$   | $CHFCF_3$   | $CF_2CFCl_2$ |
| 67 | $CF_2H$  | $CHClCF_3$ | $CF_2CF_2H$ | $CFClCF_3$   |
| 68 | $CF_3$   | $CFCl_2$   | $CFClCF_2Cl$ | $CFBrCF_3$  |
| 69 | $CF_2Cl$ | $CHFCl$    | $CCl_2CF_3$ | $CH_2CF_3$   |
| 70 | $CF_2Br$ | $CFClBr$   | $CF_2CF_3$  | $CF_2CH_3$   |

TABLE 15

R¹ = F, R² = F, R³ = H, R⁵ = OEt, n = 2, R⁴ =

|    | Column 1 | Column 2 | Column 3 | Column 4 |
|----|----------|----------|----------|----------|
| 71 | $CH_2F$  | $CHCl_2$   | $CHFCF_3$   | $CF_2CFCl_2$ |
| 72 | $CF_2H$  | $CHClCF_3$ | $CF_2CF_2H$ | $CFClCF_3$   |
| 73 | $CF_3$   | $CFCl_2$   | $CFClCF_2Cl$ | $CFBrCF_3$  |
| 74 | $CF_2Cl$ | $CHFCl$    | $CCl_2CF_3$ | $CH_2CF_3$   |
| 75 | $CF_2Br$ | $CFClBr$   | $CF_2CF_3$  | $CF_2CH_3$   |

TABLE 16

R¹ = F, R² = F, R³ = H, R⁵ = F, n = 0, R4⁴ =

|    | Column 1 | Column 2 | Column 3 | Column 4 |
|----|----------|----------|----------|----------|
| 76 | $CH_2F$  | $CHCl_2$   | $CHFCF_3$   | $CF_2CFCl_2$ |
| 77 | $CF_2H$  | $CHClCF_3$ | $CF_2CF_2H$ | $CFClCF_3$   |
| 78 | $CF_3$   | $CFCl_2$   | $CFClCF_2Cl$ | $CFBrCF_3$  |
| 79 | $CF_2Cl$ | $CHFCl$    | $Cl_2CF_3$ | $CH_2CF_3$   |
| 80 | $CF_2Br$ | $CFClBr$   | $CF_2CF_3$  | $CF_2CH_3$   |

TABLE 17

R¹ = F, R² = F, R³ = H, R⁵ = F, n = 1, R⁴ =

|    | Column 1 | Column 2 | Column 3 | Column 4 |
|----|----------|----------|----------|----------|
| 81 | $CH_2F$  | $CHCl_2$   | $CHFCF_3$   | $CF_2CFCl_2$ |
| 82 | $CF_2H$  | $CHClCF_3$ | $CF_2CF_2H$ | $CFClCF_3$   |
| 83 | $CF_3$   | $CFCl_2$   | $CFClCF_2Cl$ | $CFBrCF_3$  |

TABLE 17-continued $R^1 = F, R^2 = F, R^3 = H, R^5 = F, n = 1, R^4 =$

|  | Column 1 | Column 2 | Column 3 | Column 4 |
|---|---|---|---|---|
| 84 | $CF_2Cl$ | $CHFCl$ | $CCl_2CF_3$ | $CH_2CF_3$ |
| 85 | $CF_2Br$ | $CFClBr$ | $CF_2CF_3$ | $CF_2CH_3$ |

TABLE 18

$R^1 = F, R^2 = F, R^3 = H, R^5 = F, n = 2, R^4 =$

|  | Column 1 | Column 2 | Column 3 | Column 4 |
|---|---|---|---|---|
| 86 | $CH_2F$ | $CHCl_2$ | $CHFCF_3$ | $CF_2CFCl_2$ |
| 87 | $CF_2H$ | $CHClCF_3$ | $CF_2CF_2H$ | $CFClCF_3$ |
| 88 | $CF_3$ | $CFCl_2$ | $CFClCF_2Cl$ | $CFBrCF_3$ |
| 89 | $CF_2Cl$ | $CHFCl$ | $CCl_2CF_3$ | $CH_2CF_3$ |
| 90 | $CF_2Br$ | $CFClBr$ | $CF_2CF_3$ | $CF_2CH_3$ |

TABLE 19

$R^1 = F, R^2 = F, R^3 = H, R^5 = Cl, n = 0, R^4 =$

|  | Column 1 | Column 2 | Column 3 | Column 4 |
|---|---|---|---|---|
| 91 | $CH_2F$ | $CHCl_2$ | $CHFCF_3$ | $CF_2CFCl_2$ |
| 92 | $CF_2H$ | $CHClCF_3$ | $CF_2CF_2H$ | $CFClCF_3$ |
| 93 | $CF_3$ | $CFCl_2$ | $CFClCF_2Cl$ | $CFBrCF_3$ |
| 94 | $CF_2Cl$ | $CHFCl$ | $CCl_2CF_3$ | $CH_2CF_3$ |
| 95 | $CF_2Br$ | $CFClBr$ | $CF_2CF_3$ | $CF_2CH_3$ |

TABLE 20

$R^1 = F, R^2 = F, R^3 = H, R^5 = Cl, n = 1, R^4 =$

|  | Column 1 | Column 2 | Column 3 | Column 4 |
|---|---|---|---|---|
| 96 | $CH_2F$ | $CHCl_2$ | $CHFCF_3$ | $CF_2CFCl_2$ |
| 97 | $CF_2H$ | $CHClCF_3$ | $CF_2CF_2H$ | $CFClCF_3$ |
| 98 | $CF_3$ | $CFCl_2$ | $CFClCF_2Cl$ | $CFBrCF_3$ |
| 99 | $CF_2Cl$ | $CHFCl$ | $CCl_2CF_3$ | $CH_2CF_3$ |
| 100 | $CF_2Br$ | $CFClBr$ | $CF_2CF_3$ | $CF_2CH_3$ |

TABLE 21

$R^1 = F, R^2 = F, R^3 = H, R^5 = Cl, n = 2, R^4 =$

|  | Column 1 | Column 2 | Column 3 | Column 4 |
|---|---|---|---|---|
| 101 | $CH_2F$ | $CHCl_2$ | $CHFCF_3$ | $CF_2CFCl_2$ |
| 102 | $CF_2H$ | $CHClCF_3$ | $CF_2CF_2H$ | $CFClCF_3$ |
| 103 | $CF_3$ | $CFCl_2$ | $CFClCF_2Cl$ | $CFBrCF_3$ |
| 104 | $CF_2Cl$ | $CHFCl$ | $CCl_2CF_3$ | $CH_2CF_3$ |
| 105 | $CF_2Br$ | $CFClBr$ | $CF_2CF_3$ | $CF_2CH_3$ |

TABLE 22

$R^1 = H, R^2 = F, R^3 = H, R^5 = H, n = 0, R^4 =$

|  | Column 1 | Column 2 | Column 3 | Column 4 |
|---|---|---|---|---|
| 106 | $CF_2H$ | $CF_2Cl$ | $CF_2CF_2H$ | $CHClCF_3$ |
| 107 |  | $CF_2Br$ | $CF_2CF_3$ | $CFClCF_2Cl$ |

TABLE 23

$R^1 = F, R^2 = Cl, R^3 = H, R^5 = H, n = 0, R^4 =$

|  | Column 1 | Column 2 | Column 3 | Column 4 |
|---|---|---|---|---|
| 108 | $CF_2H$ | $CF_2Cl$ | $CF_2CF_2H$ | $CHClCF_3$ |
| 109 |  | $CF_2Br$ | $CF_2CF_3$ | $CFClCF_2Cl$ |

TABLE 24

$R^1 = Cl, R^2 = Cl, R^3 = H, R^5 = H, n = 0, R^4 =$

|  | Column 1 | Column 2 | Column 3 | Column 4 |
|---|---|---|---|---|
| 110 | $CF_2H$ | $CF_2Cl$ | $CF_2CF_2H$ | $CHClCF_3$ |
| 111 | $CF_3$ | $CF_2Br$ | $CF_2CF_3$ | $CFClCF_2Cl$ |

TABLE 25

$R^1 = H, R^2 = Cl, R^3 = H, R^5 = H, n = 0, R^4 =$

|  | Column 1 | Column 2 | Column 3 | Column 4 |
|---|---|---|---|---|
| 112 | $CF_2H$ | $CF_2Cl$ | $CF_2CF_2H$ | $CHClCF_3$ |
| 113 | $CF_3$ | $CF_2Br$ | $CF_2CF_3$ | $CFClCF_2Cl$ |

TABLE 26

$R^1 = F, R^2 = F, R^3 = F, R^5 = H, n = 0, R^4 =$

|  | Column 1 | Column 2 | Column 3 | Column 4 |
|---|---|---|---|---|
| 114 | $CF_2H$ | $CF_2Cl$ | $CF_2CF_2H$ | $CHClCF_3$ |
| 115 | $CF_3$ | $CF_2Br$ | $CF_2CF_3$ | $CFClCF_2Cl$ |

TABLE 27

$R^1 = H, R^2 = F, R^3 = F, R^5 = H, n = 0, R^4 =$

|  | Column 1 | Column 2 | Column 3 | Column 4 |
|---|---|---|---|---|
| 116 | $CF_2H$ | $CF_2Cl$ | $CF_2CF_2H$ | $CHClCF_3$ |
| 117 | $CF_3$ | $CF_2Br$ | $CF_2CF_3$ | $CFClCF_2Cl$ |

TABLE 28

$R^1 = F, R^2 = Cl, R^3 = F, R^5 = H, n = 0, R^4 =$

|  | Column 1 | Column 2 | Column 3 | Column 4 |
|---|---|---|---|---|
| 118 | $CF_2H$ | $CF_2Cl$ | $CF_2CF_2H$ | $CHClCF_3$ |
| 119 | $CF_3$ | $CF_2Br$ | $CF_2CF_3$ | $CFClCF_2Cl$ |

TABLE 29

$R^1 = Cl, R^2 = Cl, R^3 = F, R^5 = H, n = 0, R^4 =$

|  | Column 1 | Column 2 | Column 3 | Column 4 |
|---|---|---|---|---|
| 120 | $CF_2H$ | $CF_2Cl$ | $CF_2CF_2H$ | $CHClCF_3$ |
| 121 | $CF$ | $CF_2Br$ | $CF_2CF_3$ | $CFClCF_2Cl$ |

TABLE 30

$R^1 = H, R^2 = Cl, R^3 = F, R^5 = H, n = 0, R^4 =$

|  | Column 1 | Column 2 | Column 3 | Column 4 |
|---|---|---|---|---|
| 122 | $CF_2H$ | $CF_2Cl$ | $CF_2CF_2H$ | $CHClCF_3$ |
| 123 | $CF_3$ | $CF_2Br$ | $CF_2CF_3$ | $CFClCF_2Cl$ |

TABLE 31

| | |
|---|---|
| 124 | (−)-4-[4'-[(difluoromethyl)thio][1,1'-biphenyl]-4-yl]-2-(2,6-difluorophenyl)-4,5-dihydrooxazole |
| 125 | the sulfoxide of (−)4-[4'-[(difluoromethyl)thio][1,1'-biphenyl]-4-yl]-2-(2-6-difluorophenyl)-4,5-dihydrooxazole wherein the sulfoxide has the S configuration |
| 126 | the sulfoxide of (−)4-[4'-[(difluoromethyl)thio][1,1'-biphenyl]4-yl]-2-(2,6-difluorophenyl)-4,5-dihydrooxazole wherein the sulfoxide has the R configuration |
| 127 | the sulfone of (−)-4-[4'-[(difluoromethyl)thio][1,1'-biphenyl]4-yl]-2-(2-6-difluorophenyl)4,5-dihydrooxazole |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–B.

Example A

| Wettable Powder | |
| --- | --- |
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
| --- | --- |
| Compound 2 | 10.0% |
| attapulgite granules (low volatile matter, 0.71/0.30 mm; U.S.S. No. 25–50 sieves) | 90.0%. |

Example C

| Extruded Pellet | |
| --- | --- |
| Compound 2 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
| --- | --- |
| Compound 2 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), green peach aphid (*Myzus persica*), cotton aphid (*Aphis gossypii*), Russian wheat aphid (*Diuraphis noxia*), English grain aphid (*Sitobion avenae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae*, *Tetranychus cinnabarinus*, *Tetranychus mcdanieli*, *Tetranychus pacificus*, *Tetranychus turkestani*, *Byrobia rubrioculus*, *Panonychus ulmi*, *Panonychus citri*, *Eotetranychus carpini borealis*, *Eotetranychus*, *hicoriae*, *Eotetranychus sexmaculatus*, *Eotetranychus yumensis*, *Eotetranychus banksi* and *Oligonychus pratensis*; Tenuipalpidae including *Brevipalpus lewisi*, *Brevipalpus phoenicis*, *Brevipalpus californicus* and *Brevipaipus obovatus*; Eriophyidae including *Phyllocoptruta oleivora*, *Eriophyes sheldoni*, *Aculus cornutus*, *Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides, nematocides and acaricides such as abamectin, acephate, acrinathrin, alanycarb, aldicarb, aldoxycarb, alphamethrin, amitraz, avermectin, azadirachtin, azinphos-methyl, azocyclotin, bendiocarb, benfuracarb, bensultap, betacyfluthrin, bifenthrin, BPMC, brofenprox, bromophos, bufencarb, buprofezin, butocarboxim, cadusafos, carbaryl, carbofuran, carbophenothion, carbosulfan, cartap, chinomethionat, chloethocarb, chlorethoxyfos, chlorfenvinphos, chlorfenapyr (AC303630), (E)-N-[(6-chloro-3-pyridinyl) methyl]-N'-cyano-N-methyl-ethanimidamide (NI-25), chlorfluazuron, chlormephos, chlorobenzilate, chiorpyrifos, chlorpyrifos-methyl, clofentezine, cyanophos, cycloprothrin, cyfluthrin, beta-cyfluthrin, cyhalothrin, cyhexatin, cypermethrin cyromazin, deltamethrin, demeton M, demeton S, diafenthiuron, diazinon, dichlofenthion, dichlorvos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos fenpropathrin, fenamiphos, fenazaquin, fenbutatin oxide, fenitrothion, fenobucarb, fenothiocarb, fenoxycarb, fenpropathrin, fenpyroximate, fenthion, fenvalerate, fipronil, fluazinam, fluazuron (CGA 157419), flucycloxuron, flucythrinate, flufenoxuron, flufenprox, tau-fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron (CGA 184669), malathion, mecarbam, mesulfenfos, metaldehyde, methacrifos, metharnidophos, methidathion, methiocarb, methomyl, metolcarb, methoprene, methoxychlor, methyl 7-chloro-2,5-dihydro-2-[[(methoxycarbonyl)[4-(trifluoromethoxy)phenyl]amino]carbonyl]indeno[1,2-e][1,3,4]oxadiazine-4a-carboxylate (DPX-JW062), milbemectin, monocrotophos, moxidectin, omethoate, oxamyl, oxydemeton M, oxydeprofos, parathion, parathion-methyl, permethrin, phenthoate, phorate, phosalone, phosmet, phosphamidon, phoxim, pirimicarb, primiphos M, primiphos E, profenofos, promecarb, propafos, propargite, propoxur, prothiofos, prothoate, pymetrozine, pyraclofos, pyridaben, pyresmethrin, pyrethrum, pyridaben, pyrimidifen, pyriproxyfen, pymetrozine, quinalphos, remethrin, rotenone, salithion, sebuphos, silafluofen, spinosad, sulfotep, sulprofos, tebufenozide (RH 5992), tebufenpyrad, tebupirimphos, teflubenzuron, tefluthrin, temephos, terbam, terbufos, tetrachlorvinphos, thiofanox, thiodicarb, thiofanox, thiomethon, thionazin, tralomethrin, triarathene, triazophos, trichlorfon, triflumuron, trimethacarb, vamidothion, XMC, xylylcarb and zeta-cypermethrin; fungicides such as aldimorph, ampropylfos, anilazin, azaconazole, azoxystrobin (ICIA5504), benalaxyl, benodanil, benomyl, binapacryl, biphenyl, bitertanol, blasticidin-S, Bordeaux mixture (tribasic copper sulfate), bromuconazole, bupirimate, buthiobate, captafol, captan, carbendazim, carboxin, chinomethionat, chloroneb, chloropicrin, chlorothalonil, chlozolinate, copper oxychloride, copper salts, cufraneb, cyhexatin, cymoxanil, cyproconazole, cyprodinil (CGA 219417), cyprofuram, dichlorophen, diclobutrazol, diclofluanide, diclomezine, dicloran, dicofol, dienochlor, diethofencarb, difenoconazole, dimethirimol, dimethomorph, diniconazole, diniconazole-M, dinocap, diphenylarine, dipyrithione, ditalimfos, dithiazon, dodine, drazoxolon, edifenphos, epoxyconazole (BAS 480F), ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fuberidazol, furalaxyl, furmecyclox, guazatine, hexachlorobendzole, hexaconazole, hymexazol, imazalil, imibenconazole, iminoctadine, ipconazole, iprobenfos, iprodione, isoprothiolane, kasugamycin, kresoxim-methyl (BAS 490F), mancopper, mancozeb, maneb, mepanipyrim, mepronil, metalaxyl, metconazole, methasulfocarb, methfuroxam, (E)-2-(methoxyimino)-N-methyl-2-(2-phenoxyphenyl)acetamidemetiram (SSF-126), metsulfovax, myclobutanil, neo-asozin (ferric methanearsonate), nitrothal-isopropyl, nuarimol, ofurace, oxadixyl, oxycarboxin, pefurazoate, penconazole, pencycuron, phosdiphen, phthalide, pimaricin, piperalin, polycarbamate, polyoxin, probenazole, prochloraz, procymidone, propamocarb. propiconazole, propineb, pyrazophos, pyrifenox, pyrimethanil, pyroquilon, quintozen, sulfur, tebuconazole, tecloftalame, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizol, triforin, triticonazole, uniconazole, validamycin, vinclozolin, zineb, and ziram; bactericides such as streptomycin; and biological agents such as *Bacillus thuringiensis, Bacillus thiuringiensis* delta endotoxin, baculovirus, and entomopathogenic bacteria, virus and fungi.

In certain instances, combinations with other arthropodicides having a similar spectrum of control but a different mode of action will be particularly advantageous for resistance management.

Preferred for better control of pests (use rate or spectrum) or resistance management are mixtures of a compound of this invention with an arthropodicide selected from the group abamectin, fenpropathrin, fipronil, imidacloprid, methomyl, propargite, pyridaben, tebufenozide and tebufenpyrad. Specifically preferred mixtures (compound numbers refer to compounds in Index Tables A–B) are selected from the group: compound 2 and abamectin; compound 2 and fenpropathrin; compound 2 and fipronil; compound 2 and imidacloprid; compound 2 and methomyl; compound 2 and propargite; compound 2 and pyridaben; compound 2 and tebufenozide; compound 2 and tebufenpyrad; compound 3 and abamectin; compound 3 and fenpropathrin; compound 3 and fipronil; compound 3 and imidacloprid; compound 3 and methomyl; compound 3 and propargite; compound 3 and pyridaben; compound 3 and tebufenozide; compound 3 and tebufenpyrad; compound 4 and abamectin; compound 4 and fenpropathrin; compound 4 and fipronil; compound 4 and imidacloprid; compound 4 and methomyl; compound 4 and propargite; compound 4 and pyridaben; compound 4 and tebufenozide; and compound 4 and tebufenpyrad.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of the invention, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Tables A–B for compound descriptions. The following abbreviations are used in the Index Tables which follow: Me=methyl, Et=ethyl, OMe=methoxy, and OEt=ethoxy.

INDEX TABLE A

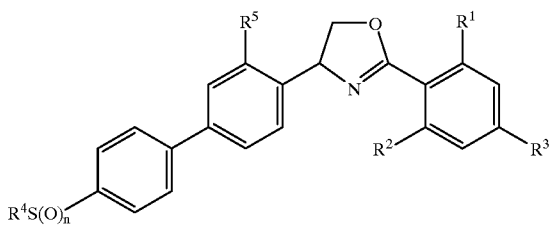

| Cmpd No. | $R^1$ | $R^2$ | $R^3$ | $R^4$ | $R^5$ | n | m.p.(° C.) |
|---|---|---|---|---|---|---|---|
| 1 | F | F | H | $CH_2F$ | H | 0 | 107–109 |
| 2(Ex. 1) | F | F | H | $CF_2H$ | H | 0 | 72–76 |
| 3 | F | F | H | $CF_2H$ | H | 1 | 71–72 |
| 4 | F | F | H | $CF_2H$ | H | 2 | 115–117 |
| 5 | F | F | H | $CH_2F$ | H | 1 | solid* |
| 6 | F | F | H | $CH_2F$ | H | 2 | solid* |
| 7 | F | F | H | $CF_2H$ | OEt | 0 | oil* |
| 8 | F | F | H | $CF_2H$ | OMe | 0 | oil* |
| 9 | F | F | H | $CH_2CF_3$ | H | 0 | solid* |
| 10 | F | F | H | $CF_2Br$ | H | 0 | 100–102 |
| 11 | F | F | H | $CFClCF_2Cl$ | H | 0 | 90–92.5 |
| 12 | F | F | H | $CF_2Cl$ | H | 0 | solid* |
| 13 | F | F | H | $CF_2CF_3$ | H | 0 | 101–104 |
| 14 | F | F | H | $CF_2H$ | Me | 0 | oil* |
| 15 | F | F | H | $CF_3$ | Me | 0 | solid* |
| 16 | Cl | H | H | $CF_2H$ | H | 0 | 59–62 |
| 17 | F | H | H | $CF_2H$ | H | 0 | 70–76 |
| 18 | Cl | Cl | H | $CF_2H$ | H | 0 | 96–100 |
| 19 | Cl | F | H | $CF_2H$ | H | 0 | oil* |
| 20 | Cl | H | H | $CF_2H$ | H | 1 | gum* |
| 21 | Cl | H | H | $CF_2H$ | H | 2 | solid* |
| 22 (+) isomer | F | F | H | $CF_2H$ | H | 0 | 77–78 |
| 23 (−) isomer | F | F | H | $CF_2H$ | H | 0 | 71–73 |

*See Index Table B for $^1$H NMR data.

INDEX TABLE B

| Cmpd No. | $^1$H NMR Data ($CDCl_3$ solution unless indicated otherwise)[a] |
|---|---|
| 5 | δ 4.4 (m, 1H), 4.8–4.9 (m, 1H), 5.1–5.3 (m, 2H), 5.5–5.6 (m, 1H), 7.0 (m, 2H), 7.4–7.5 (m, 3H), 7.6 (m, 2H), 7.7–7.8 (m, 4H). |
| 6 | δ 4.3–4.4 (m, 1H), 4.9 (m, 1H), 5.1–5.3 (m, 2H), 5.5–5.6 (m, 1H), 7.0 (m, 2H), 7.4–7.5 (m, 3H), 7.6 (m, 2H), 7.8 (m, 2H), 8.0 (m, 2H). |
| 7 | δ 1.4–1.5 (t, 3H), 4.1–4.2 (q, 2H), 4.2 (m, 1H), 4.9 (m, 1H), 5.7–5.8 (m, 1H), 6.85 (t, 1H), 7.0–7.1 (m, 3H), 7.2 (m, 1H), 7.4 (m, 1H), 7.5 (m, 1H), 7.6–7.7 (m, 4H). |
| 8 | δ 3.9 (s, 3H), 4.2 (m, 1H), 4.9 (m, 1H), 5.7 (m, 1H), 6.85 (t, 1H), 7.0–7.1 (m, 3H), 7.2 (m, 1H), 7.4 (m, 1H), 7.5 (m, 1H), 7.6–7.7 (m, 4H). |

INDEX TABLE B-continued

| Cmpd No. | $^1$H NMR Data ($CDCl_3$ solution unless indicated otherwise)[a] |
|---|---|
| 9 | δ 3.4–3.5 (m, 2H), 4.3 (m, 1H), 4.8 (m, 1H), 5.5 (m, 1H), 7.0 (m, 2H), 7.2–7.6 (m, 9H). |
| 12 | δ 4.3–4.4 (m, 1H), 4.8–4.9 (m, 1H), 5.5 (m, 1H), 7.0 (m, 2H), 7.4–7.5 (m, 3H), 7.6–7.8 (m, 6H). |
| 14 | δ 2.4 (s, 3H), 4.2 (m, 1H), 4.9 (m, 1H), 5.7 (m, 1H), 6.85 (t, 1H), 7.0 (m, 2H), 7.4–7.6 (m, 4H), 7.6–7.7 (m, 4H). |
| 15 | δ 2.4 (s, 3H), 4.2 (m, 1H), 4.9 (m, 1H), 5.7 (m, 1H), 7.0 (m, 2H), 7.4–7.5 (m, 4H), 7.6–7.7 (m, 2H), 7.7 (m, 2H). |
| 19 | δ 4.4 (m, 1H), 4.9 (m, 1H), 5.6 (m, 1H), 6.86 (t, 1H), 7.1 (m, 1H), 7.3 (m, 1H), 7.4 (m, 1H), 7.4–7.5 (m, 2H), 7.6–7.7 (m, 6H). |
| 20 | δ 4.3–4.4 (m, 1H), 4.8–4.9 (m, 1H), 5.5 (m, 1H), 6.1 (t, 1H), 7.3–7.4 (m, 1H), 7.4 (m, 1H), 7.5 (m, 3H), 7.6 (m, 2H), 7.8 (m, 4H), 7.9 (m, 1H). |
| 21 | δ 4.3 (m, 1H), 4.9 (m, 1H), 5.5 (m, 1H), 6.2 (t, 1H), 7.3 (m, 1H), 7.4 (m, 1H), 7.5 (m, 3H), 7.6–7.7 (m, 2H), 7.8–7.9 (m, 3H), 8.0–8.1 (m, 2H). |

[a]$^1$H NMR data are in ppm downfield from tetramethylsilane. Couplings are designated by (s)-singlet, (t)-triplet, (q)-quartet, (m)-multiplet.

BIOLOGICAL EXAMPLES OF THE INVENTION

Test A

Larval two-Spotted Spider Mites (*Tetranychus urticae*)

Solutions of the test compounds were prepared by dissolving in a minimum of acetone and then adding water containing a wetting agent until the concentration of the compound was 50 ppm. Two-week old red kidney bean plants infested with two-spotted spider mites eggs were sprayed to run-off (equivalent to 28 g/ha) with the test solution using a turntable sprayer. Plants were held in a chamber at 25° C. and 50% relative humidity. Of the compounds tested, the following gave larvicide/ovicide activity of 80% or higher seven days after spraying: 1, 2, 3, 4, 5, 6, 7, 8, 9*, 10*, 11*, 12**, 13*, 14*, 15*, 16, 17, 18**, 19* and 23**.

* Compound was sprayed at a concentration of 5 ppm (equivalent to 2.8 g/ha).
** Compound was sprayed at a concentration of 0.5 ppm (equivalent to 0.28 g/ha).

Test B

Fall Armyworm Whole Plant Test

Solutions of the test compounds were prepared by dissolving in a minimum of acetone and adding water containing a wetting agent until the concentration of the compounds was 10 ppm. Test compounds were then sprayed to run-off (equivalent to 5.5 g/ha) onto soybean plants utilizing a rotating platform and an atomizing sprayer. Treated plants were dried, and fall armyworm (*Spodoptera frugiperda*) larvae were exposed to excised, treated leaves. Test units were held at 27° C. and 50% relative humidity, and evaluated for larval mortality 120 h post-infestation. Of the compounds tested, the following gave mortality levels of 80% or higher: 2*, 3*, 4*, 5, 6, 7, 8, 9, 10, 11, 12, 13, 14, 15, 16*, 17*, 18*, 19 and 23**.

* Compound was sprayed at a concentration of 3 ppm (equivalent to 1.6 g/ha).
** Compound was sprayed at a concentration of 0.3 ppm (equivalent to 0.16 g/ha).

What is claimed is:

1. A compound selected from Formula I, and agriculturally suitable salts thereof,

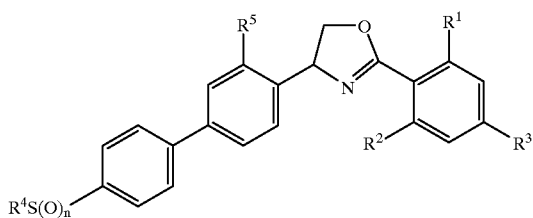

wherein:
R¹ is H, F, or Cl;
R² is F or Cl;
R³ is H or F;
R⁴ is $C_1$–$C_2$ haloalkyl;
R⁵ is H, F, Cl, $C_1$–$C_2$ alkyl, or $C_1$–$C_2$ alkoxy; and
n is 0, 1, or 2;
provided that
  i) when R² is F, R³ and R⁵ are H, and n is 0, then R⁴ is other than $CF_3$; and
  ii) when R¹ is F, R² is Cl, R³ and R⁵ are H, and n is 0, then R⁴ is other than $CF_3$.

2. A compound of claim 1 wherein:
R¹ and R² are F;
R³ is H; and
R⁴ is $CF_2H$, $CF_3$, $CF_2Br$, $CF_2CF_2H$, or $CF_2CF_3$.

3. A compound of claim 1 wherein:
R¹, R² and R³ are F; and
R⁴ is $CF_2H$, $CF_3$, $CF_2Br$, $CF_2CF_2H$, or $CF_2CF_3$.

4. A compound of claim 1 wherein:
R¹ is H;
R² is Cl; and
R⁵ is H.

5. The compound of claim 4 which is selected from the group:
  2-(2-chlorophenyl)-4-[4'-[(difluoromethyl)thio][1,1'-biphenyl]-4-yl]-4,5-dihydrooxazole;
  2-(2-chlorophenyl)-4-[4'-[(difluoromethyl)sulfinyl][1,1'-biphenyl]-4-yl]-4,5-dihydrooxazole; and
  2-(2-chlorophenyl)-4-[4'-[(difluoromethyl)sulfonyl][1,1'-biphenyl]-4-yl]-4,5-dihydrooxazole.

6. A compound of claim 2 wherein:
R⁵ is H.

7. A compound of claim 6 wherein:
R⁴ is $CF_2H$, $CF_3$ or $CF_2Br$.

8. The compound of claim 7 which is selected from the group:
  4-[4'-[(difluoromethyl)thio][1,1'-biphenyl]-4-yl]-2-(2,6-difluorophenyl)-4,5-dihydrooxazole;
  4-[4'-[(difluoromethyl)sulfinyl][1,1'-biphenyl]-4-yl]-2-(2,6-difluorophenyl)-4,5-dihydrooxazole; and
  4-[4'-[(difluoromethyl)sulfonyl][1,1'-biphenyl]-4-yl]-2-(2,6-difluorophenyl)-4,5-dihydrooxazole.

9. The compound of claim 8 which is
  4-[4'-[(difluoromethyl)thio][1,1'-biphenyl]-4-yl]-2-(2,6-difluorophenyl)-4,5-dihydrooxazole.

10. The compound of claim 8 which is
  4-[4'-[(difluoromethyl)sulfinyl][1,1'-biphenyl]-4-yl]-2-(2,6-difluorophenyl)-4,5-dihydrooxazole.

11. The compound of claim 8 which is
  4-[4'-[(difluoromethyl)sulfonyl][1,1'-biphenyl]-4-yl]-2-(2,6-difluorophenyl)-4,5-dihydrooxazole.

12. The compound of claim 9 which is
  (−)-4-[4'-[(difluoromethyl)thio][1,1'-biphenyl]-4-yl]-2-(2,6-difluorophenyl)-4,5-dihydrooxazole.

13. The compound of claim 10 which is the sulfoxide of (−)-4-[4'-[(difluoromethyl)thio][1,1'-biphenyl]-4-yl]-2-(2,6-difluorophenyl)-4,5-dihydrooxazole wherein the sulfoxide has the S configuration.

14. The compound of claim 10 which is the sulfoxide of (−)-4-[4'-[(difluoromethyl)thio][1,1'-biphenyl]-4-yl]-2-(2,6-difluorophenyl)-4,5-dihydrooxazole wherein the sulfoxide has the R configuration.

15. The compound of claim 11 which is the sulfone of (−)-4-[4'-[(difluoromethyl)thio][1,1'-biphenyl]-4-yl]-2-(2,6-difluorophenyl)-4,5-dihydrooxazole.

16. An arthropodicidal composition comprising an arthropodicidally effective amount of a compound of claim 1 and at least one of a surfactant, a solid diluent or a liquid diluent.

17. A method for controlling arthropods comprising contacting the arthropods or their environment with an arthropodicidally effective amount of a compound of claim 1.

* * * * *